United States Patent [19]
Ogawa et al.

[11] Patent Number: 5,466,486
[45] Date of Patent: Nov. 14, 1995

[54] CHEMICALLY ADSORBED MONOMOLECULAR LAMINATION FILM

[75] Inventors: Kazufumi Ogawa, Hirakata; Norihisa Mino, Settsu; Mamoru Soga, all of Osaka, Japan

[73] Assignee: Matsushita Electric Industrial Co., Ltd., Kadoma, Japan

[21] Appl. No.: 316,105

[22] Filed: Sep. 30, 1994

Related U.S. Application Data

[62] Division of Ser. No. 37,727, Mar. 26, 1993, Pat. No. 5,380,585, which is a continuation of Ser. No. 781,407, Oct. 23, 1991, abandoned.

[30] Foreign Application Priority Data

| Oct. 25, 1990 | [JP] | Japan | 2-289128 |
| Dec. 25, 1990 | [JP] | Japan | 2-405754 |
| Jan. 23, 1991 | [JP] | Japan | 3-024025 |
| Jan. 23, 1991 | [JP] | Japan | 3-024026 |
| Jan. 28, 1991 | [JP] | Japan | 3-008321 |
| Feb. 6, 1991  | [JP] | Japan | 3-038137 |

[51] Int. Cl.$^6$ .................................................. B05D 3/02
[52] U.S. Cl. ............................ 427/352; 427/353; 427/354; 427/387
[58] Field of Search ............................ 427/387, 430.1, 427/352, 353, 354; 428/420

[56] References Cited

U.S. PATENT DOCUMENTS

| 4,539,061 | 9/1985 | Sagiv | 156/278 |
| 4,673,474 | 6/1987 | Ogawa | 428/910 X |
| 4,824,766 | 4/1989 | Ogawa | 430/299 |
| 4,992,300 | 2/1991 | Ogawa | 427/128 X |
| 5,139,928 | 8/1992 | Lewis | 430/270 X |

FOREIGN PATENT DOCUMENTS 0474228  5/1991  European Pat. Off. .

OTHER PUBLICATIONS

Netzer et al., "Thin Solid Films" 99:235–241 (1983).
Japan Society of Applied Physics Catalog No.: AP 90110–03.
Ogawa et al., "Langmuir" 6(4):851–856 (1990).
Mullin et al., "The American Physical Society", 39(7):3745–3747 (Apr. 1, 1989).
Netzer et al., "J. Am. Chem Soc." 105:674–676 (1983).
World Patents Index Latest, Derwent Publications Ltd., London, GB; AN 90–120634 & JP–A–2 071 873.

*Primary Examiner*—Michael Lusignan
*Attorney, Agent, or Firm*—Fish & Richardson

[57] ABSTRACT

The invention to provide a chemically adsorbed monomolecular lamination film comprising a chemically adsorbed monomolecular film formed via a siloxane-based monomolecular or polymer film on a substrate surface. It also seeks to provide a method of forming a chemically adsorbed monomolecular film efficiently and with high density on a substrate surface with few hydroxyl groups, which method comprises a step of contacting a substrate containing hydroxyl groups present on the surface with a non-aqueous solution containing a material with plural chlorosilanol groups in molecule, a step of removing the material remaining on the substrate without reaction by washing the substrate with a non-aqueous organic solution (if this process is omitted, the siloxane-based polymer film is prepared on the substrate), a step of forming a monomolecular film constituted by a compound containing a silanol group in molecule on the substrate by exposing to the air containing moisture or washing with water, after the removal step, and a step of laminating a monomolecular adsorption film by adsorbing a chlorosilane-based surface active agent constituted by a straight hydrocarbon chain having a chlorosilane groups at one end onto the substrate after the monomolecular or polymer film formation step.

8 Claims, 3 Drawing Sheets

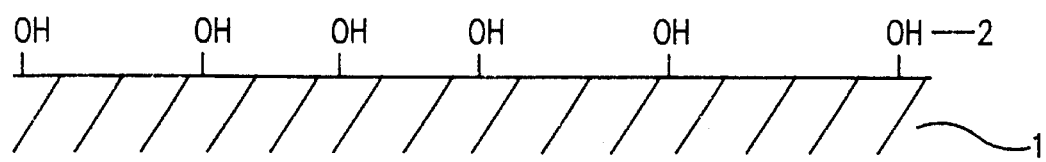
FIG. I(a)
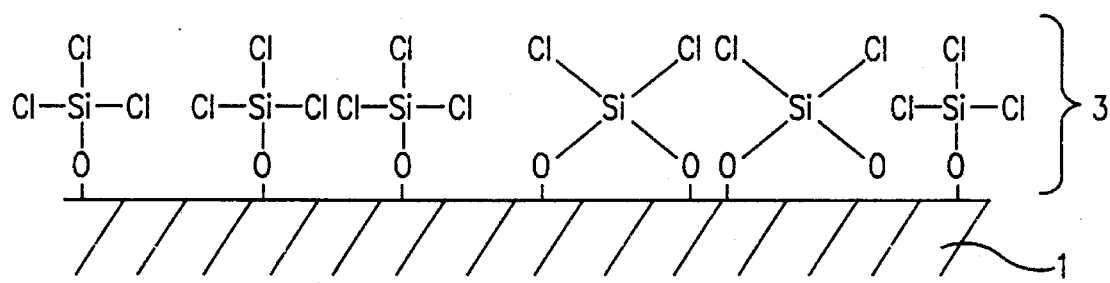
FIG. I(b)
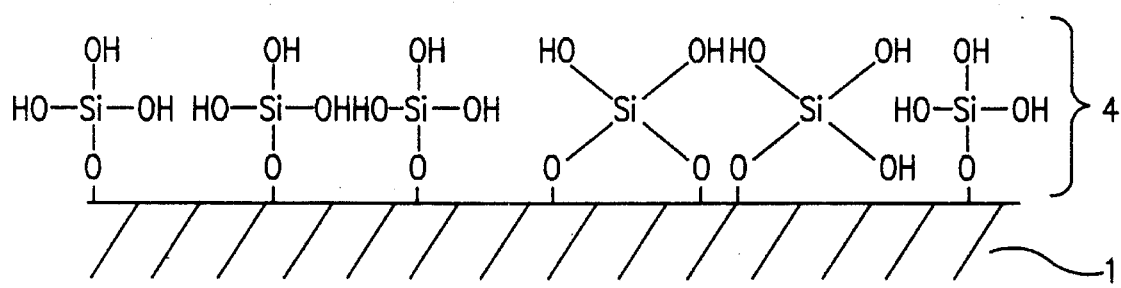
FIG. I(c)

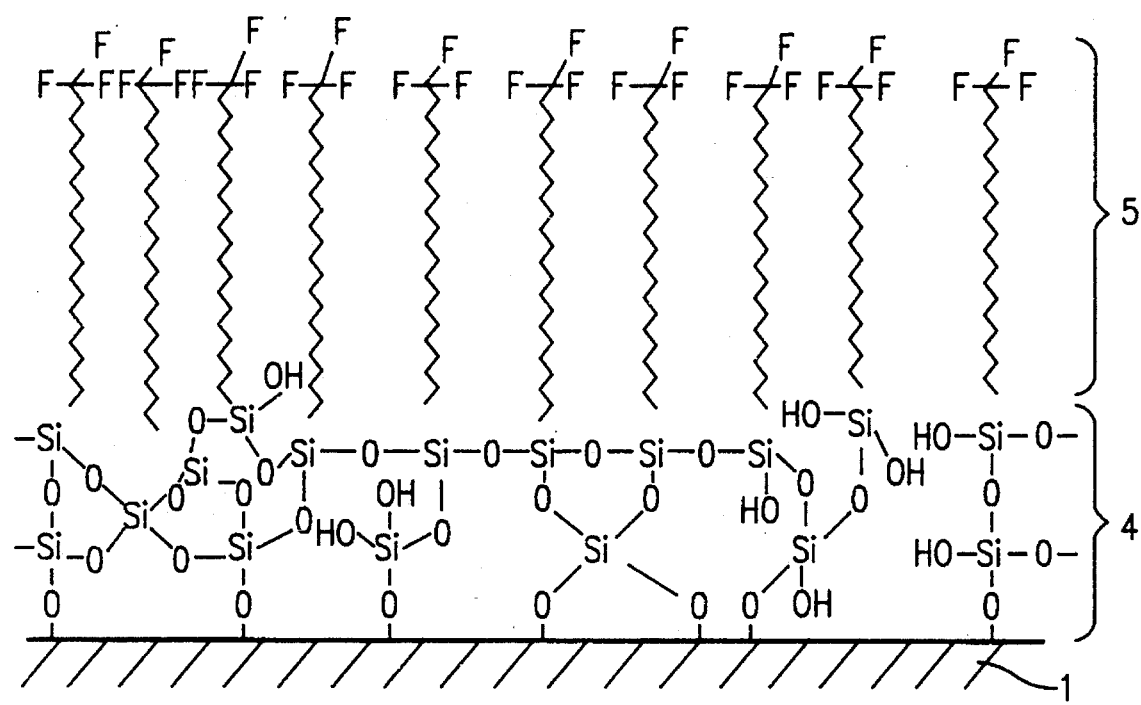
FIG. I(d)

CHEMICALLY ADSORBED MONOMOLECULAR LAMINATION FILM

This application is a division of U.S. patent application Ser. No. 08/037,727, filed Mar. 26, 1993, now U.S. Pat. No. 5,380,585, which is a continuation of 07/781,407, filed Oct. 23, 1991, now abandoned.

FIELD OF THE INVENTION

This invention relates to chemically adsorbed monomolecular films and, more particularly, to a chemically adsorbed film, which comprises a chemically adsorbed monomolecular film laminated on a siloxane-based polymer film or a siloxane-based chemically adsorbed monomolecular film, and also a method of manufacturing the same.

BACKGROUND OF THE INVENTION

A monomolecular film may be formed by a chemical adsorption process as is well known in the art.

The principles underlying the manufacture of a chemically adsorbed monomolecular film reside in forming a monomolecular film by making use of a hydrochloric acid removal reaction between hydroxyl groups on a substrate surface and chlorosilyl groups of a chlorosilane-based surface active agent.

It has been impossible to form a film on a substrate which has no hydroxyl group present on the surface, such as a plastic substrate.

Further, with a substrate having hydroxyl groups present at a low density on the surface, such as aluminum and stainless steel substrates, it is impossible to form a perfect adsorption film in a short period of time because of the low density of hydroxyl groups.

Accordingly, to form a chemically adsorbed film on the surface of an aluminum or stainless steel substrate, the surface of the substrate has, in practice, been oxidized to introduce hydroxyl groups.

Meanwhile, the surface of an aluminum or stainless steel substrate is rendered heat-resistant, weather-resistant and wear-resistant by coating the substrate surface with a fluorocarbon-based thin film.

This is usually done by rendering the surface of an aluminum substrate, or the like, coarse by means of a wire brush or chemical etching, coating with a primer or the like and then with a paint prepared by suspending fluorocarbon-based fine particles of ethylene polytetrafluoride or the like in ethanol or the like, followed by drying and then baking at 400° C. for about one hour, thus fixing a fluorocarbon-based polymer on the substrate surface.

The prior art method, in which the surface of an aluminum or stainless steel substrate is oxidized to introduce hydroxyl groups to the substrate surface so as to obtain a perfect chemically adsorbed film, however, does not have a substantially high effect of increasing hydroxyl groups. Typically, the formation of a perfect adsorption film requires an adsorbing operation at room temperature for about 100 hours. Besides, the substrate surface becomes coarse.

The prior art method of manufacturing (or coating) a fluorocarbon-based coating film, on the other hand, permits ready formation of the film. However, since the polymer is in close contact with the substrate with the sole anchoring effect, is a limit on the close contact of the polymer with the substrate. Therefore, the performance of the method is insufficient when used for manufacturing high mechanical strength apparatuses and the like requiring heat-resistant, weather-resistant and wear-resistant coatings, for instance hot plates, rice cookers and other electric products, vehicles, industrial machines, glass lenses and mirrors.

Moreover, with the prior art coating method a coating film thickness of at least several ten microns is necessary in order to prevent generation of pin-holes.

SUMMARY OF THE INVENTION

The present invention has been developed in light of the above drawbacks in the prior art, and its objective vide a chemically adsorbed monomolecular film comprising a chemically adsorbed film efficiently formed on a substrate surface with less hydroxyl groups and a method of manufacturing the same.

The primary objective of this invention is to provide a chemically adsorbed monomolecular lamination film comprising a siloxane-based film formed on a substrate surface by chemical bonding thereto and a chemically adsorbed monomolecular film formed on the siloxane-based film.

Another objective of this invention is to provide a method of manufacturing a chemically adsorbed monomolecular lamination film comprising:

a step of contacting a substrate having hydroxyl groups on the surface with a non-aqueous solution containing a material having plural chlorosilane groups in molecule;

a step of removing the material remaining on the substrate without reaction by washing the substrate using a non-aqueous organic solvent;

a step of forming a siloxane-based film constituted with a compound containing a silanol group in molecule on the substrate by reacting the chlorosilane grouped with water after the removing step; and a step of laminating a adsorbed monomolecular film by adsorbing a chlorosilane-based surface active agent having a straight hydrocarbon chain and a chlorosilane group at one end onto the substrate after the siloxane-based film formation step.

Yet another objective of this invention is to provide a method of manufacturing a chemically adsorbed monomolecular lamination film comprising:

a step of contacting a substrate having hydroxyl groups on the surface with a non-aqueous solution containing a material having plural chlorosilane groups in molecule:

a step of forming a siloxane-based film constituted with a compound containing a silanol group in molecule on the substrate by reacting the chlorosilane grouped with water after the removing step; and a step of laminating a adsorbed monomolecular film by adsorbing a chlorosilane-based surface active agent having a straight hydrocarbon chain and a chlorosilane group at one end onto the substrate after the siloxane-based film formation step.

It is preferable in this invention that the siloxane-based film is a siloxane-based monomolecular film.

It is preferable in this invention that the chemically adsorbed monomolecular film contains fluorine.

It is preferable in this invention that the chemically adsorbed monomolecular film contains hydrocarbon chain.

It is preferable in this invention that the substrate surface and the siloxane-based monomolecular film are bonded with covalent bonds, and the siloxane-based monomolecular film and the chemically adsorbed monomolecular film are bonded with covalent bonds.

It is preferable in this invention that the substrate is made of a member of a group consisting of metals, ceramics and plastics.

It is preferable in this method invention that the substrate is made of a member of a group consisting of metals and ceramics.

It is preferable in this method invention that the substrate is a plastic substrate with the surface having been made hydrophilic in advance by a treatment in a plasma or corona atmosphere containing oxygen.

It is preferable in this method invention that the material having a chlorosilyl group in molecule is a member of a group consisting of $SiCl_4$, $SiHCl_3$, $SiH_2Cl_2$ and $Cl-(SiCl_2O)_n-SiCl_3$ where n is an integer.

It is preferable in this method invention that the hydrocarbon chain of the chlorosilane-based surface active agent is partly substituted for by a $-CF_2-$ group.

It is preferable in this method invention that the chlorosilane-based surface active agent is $CF_3-(CF_2)_n-(R)_m-SiX_pCl_{3-p}$ where n represents 0 or an integer, R represents an alkyl group or a substitute group containing a C=C, a C≡C, a silicon atom or an oxygen atom, m represents 0 or 1, X represents a hydrogen atom or a substitute group in a group consisting of an alkyl group, an alkoxy group, a fluorine-containing alkyl group and a fluorine-containing alkoxy group, and p represents 0, 1 or 2.

BRIEF DESCRIPTION OF THE DRAWINGS

This invention will now be described in detail with reference to the following drawings.

FIGS. 1(a), 1(b), 1(c) and 1(d) are schematic sectional views showing steps of a process of laminating an organic monomolecular film of Example 1 of this invention.

DETAILED DESCRIPTION OF THE INVENTION

Figure 2:
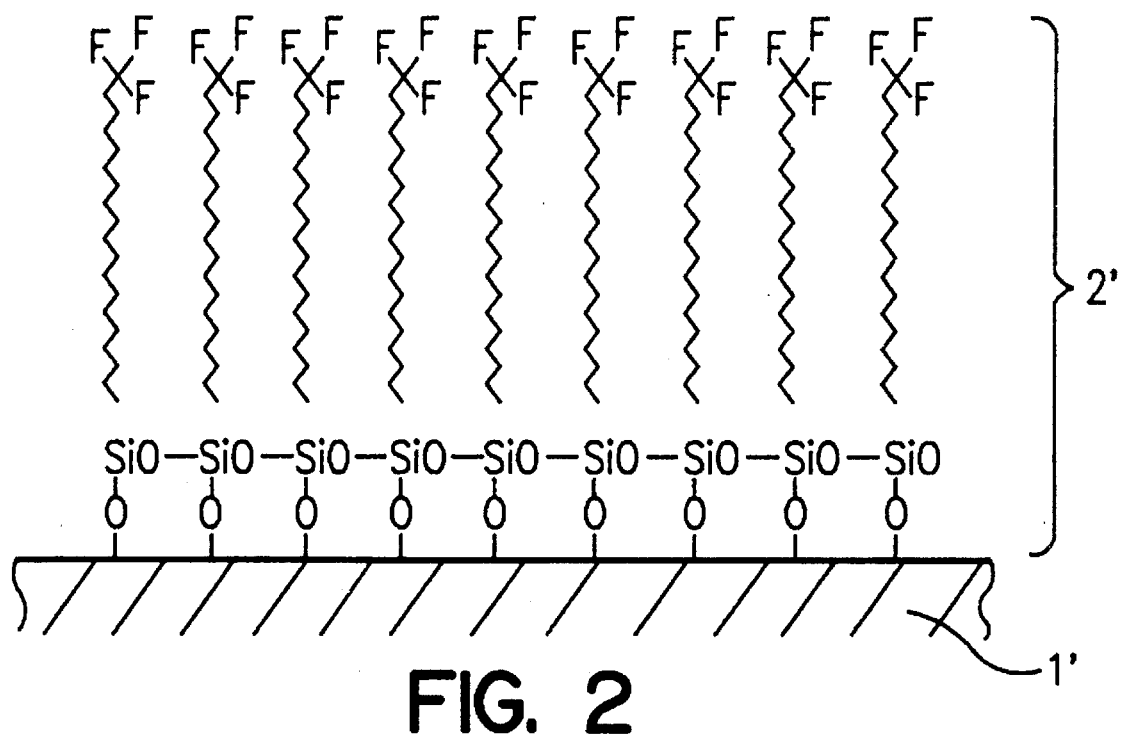
FIGS. 2, 3 and 4 are schematic sectional showing steps of a process of laminating an organic monomolecular film of Example 2 of this invention.
Figure 3:
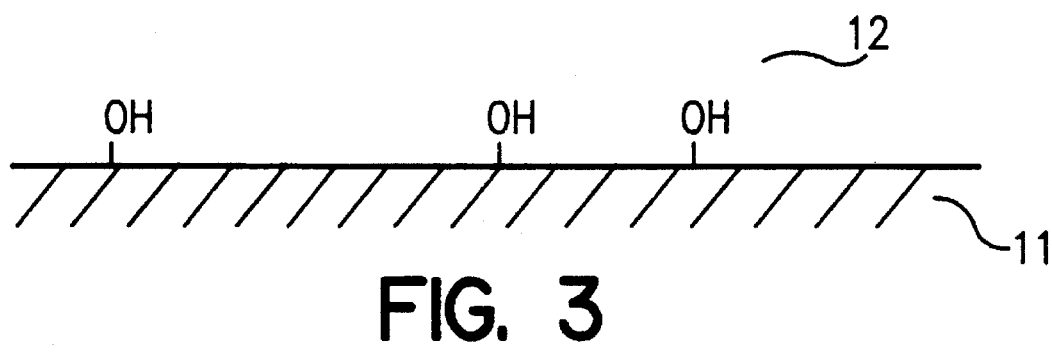

The invention is to provide a method, which permits formation of a fluorocarbon-based monomolecular film with satisfactory close contact with respect to the substrate, pinhole-free and thinly, thus improving the performance of apparatuses or the like requiring heat-resistant, weather-resistant and wear-resistant coatings such as hot plates, rice cookers and other electric products, vehicles, industrial apparatuses, glass lenses and mirrors.

To attain the above objective of the invention, there are provided, a chemically adsorbed monomolecular lamination film, which comprises a chemically adsorbed monomolecular film formed via a siloxane-based monomolecular or polymer film on a substrate surface, and a method of forming a chemically adsorbed monomolecular lamination film, which comprises a step of contacting a substrate having hydroxyl groups on the surface with a non-aqueous solution containing a material with a chlorosilane group in a molecule, a step of removing the material remaining on the substrate without reaction by washing the substrate with a non-aqueous organic solution (at this time, if this process is omitted, a siloxane-based polymer film is prepared on the substrate), a step of forming a monomolecular film constituted by a compound containing a silanol group in molecule on the substrate after the removal step by exposing the substlate to the air containing moisture, and a step of laminating a monomolecular adsorption film by causing chemical adsorption of a chlorosilane-based surface active agent constituted by straight hydrocarbon chain molecules having a chlorosilane group at one end onto the substrate after the first monomolecular film formation step.

According to the invention, a siloxane-based monomolecular film having a siloxane ($-SiOH$) group in the film may be formed on even a substrate which hardly has hydroxyl groups present on the surface, by holding the substrate dipped in a non-aqueous solution containing a material with a chlorosilyl group in molecule to bring about a reaction between hydroxyl groups on the substrate surface and chlorosilyl groups of the material. The extra remaining material having chlorosilyl groups is removed without reaction on the substrate by washing the substrate with a non-aqueous organic solvent, followed by washing the substrate with water or exposing the substrate to the air containing moisture.

$-SiOH$ bonds are formed on the substrate surface at this time, and they are bonded to the substrate via siloxane bonds. Accordingly, by subsequently causing chemical adsorption of another monomolecular film onto the monomolecular film having the SiOH bonds, by using a non-aqueous solution containing a silane-based surface active agent containing a chlorosilane group in molecule, a hydrochloric acid removal reaction is brought about between $-OH$ groups of the polysiloxane-based monomolecular film, having been formed on the substrate surface in the previous step and having many SiOH groups, and chlorosilyl groups of the silane-based surface active agent, thus forming a monomolecular film chemically bonded via $-SiO-$ bonds to the substrate.

For example, a substrate contains few hydroxyl groups although it is hydrophilic, such as those made of such metals as Al, Cu and stainless steel or plastic substrates with the surface rendered to be hydrophilic.

In the chemically adsorbed monomolecular film according to the invention, hydrophilic groups present on the surface of the substrate and chlorosilyl groups react each other. Therefore, when using a metal for the substrate, metals commonly called base metals are suitable.

In case of a plastic or like material which does not have any oxide film on the surface, it may be rendered to be hydrophilic, i.e., hydroxyl groups may be introduced onto it, in advance through a treatment of the surface in a plasma atmosphere containing oxygen at 100 W for 20 minutes or a corona treatment of the surface. However, a plastics having $-NH$ groups such as polyamide or polyurethane substrates are not necessary a surface oxygen treatment. For reason, as $-NH$ groups have active hydrogen, it is easy to cause the dehydrochloric acid reaction with chlorosilyl groups of surface active agent.

A material containing a chlorosilyl group may be used according to the invention, $SiCl_4$, $SiHCl_3$, $SiH_2Cl_2$, $Cl-(SiCl_2O)_n-SiCl_3$ where n is an integer and n is preperably in a range of 1 to 22, are suitable.

In particular, $SiCl_4$ is preferred because its molecule is small and highly active with respect to the hydroxyl group, thus having a great effect of uniformly rendering the substrate surface to be hydrophilic.

The solution containing the material with a trichlorosilyl group may, for instance, be a non-aqueous solution containing chloroform.

The concentration of the material containing a trichlorosylil group in a molecule in the non-aqueous solution varies with the kind of the material containing a trichlorosylil group in the molecule that is used or the solution containing such material, but a solution prepared by dissolving about one per cent by weight of the material is used. By dipping the substrate in this solution for about 30 minutes, a hydrochloric acid removal reaction is brought out on the surface because of the presence of some hydrophilic —OH groups on the surface of the substrate, and thus a chlorosilane monomolecular film having the material containing a trisilyl group in molecule is formed.

As the compound having a chlorosilyl group in molecule, $SiCl_4$, $SiHCl_3$, $SiH_2Cl_2$, or $Cl-(SiCl_2O)_n-SiCl_3$ where n is an integer, may be used. By bonding the chlorosilyl group with a functional group, for example —OH group, the substrate may be imparted with a functional property owing to the functional group. Examples of the functional group are compounds containing a florocarbon group and a chlorosilane group in a molecule, and specifically $CF_3-(CF_2)_n-(R)_mSiX_pCl_{3-p}$ where n represents 0 or an integer, n is preferably in a range of 1 to 22, R represents an alkyl group or a substitute group containing a C=C, a C≡C, a silicon atom or a hydrogen atom, m represents 0 or 1, X represents a hydrogen atom or substitute group in a group consisting of an alkyl group, alkoxy group, a fluorine-containing alkyl group or a fluorine-containing alkoxy group, and p represents 0, 1 or 2. The compound containing a fluorcarbon group may be used suitably for it can impart a hydrophobic property, an oil-repelling property and lubricity.

Other examples of the functional group are compounds containing a hydrocarbon group and a chlorosilane group in a molecule, and specifically such as formulas;

$$CH_3-(CH_2)_rSiX_pCl_{3-p}$$

$$CH_3(CH_2)_sO(CH_2)_tSiX_pCl_{3-p},$$

$$CH_3(CH_2)_u-Si(CH_3)_2(CH_2)_v-SiX_pCl_{3-p},$$

$$CF_3COO(CH_2)_wSiX_pCl_{3-p}$$

(Where r represents 1 to 25, s represents 0 to 12, t represents 1 to 20, u represents 0 to 12, v represents 1 to 20, w represents 1 to 25.) As the hydrocarbon-based surface active agent for example:

$$CH_3CH_2O(CH_2)_{15}SiCl_3,$$

$$CH_3(CH_2)_2Si(CH_3)_2(CH_2)_{15}SiCl_3,$$

$$CH_3(CH_2)_6Si(CH_3)_2(CH_2)_9SiCl_3,$$

$CH_3COO(CH_2)_{15}SiCl_3$ may be used in addition to the agent noted above.

The invention can widely be applied to the following uses. Materials made of metal, cermic, glass, plastic, wood, stone etc. are applicable to the substrate. The surface of the substrate can also be coated with paint or the like.

Examples of cutlery: a kitchen knife, scissors, a knife, a cutter, a graner, a razor, hair clippers, a saw, a plane, a chisel, a gimlet, a badkin, bite (cutting tools), the edge of a drill, the edge of a mixer and juicer brade, a blade of a mill, a blade of a lawnmower, a punch, a straw cutter, a staple of a stapler, a can opener or a surgical knife and the like.

Examples of needles: an acupuncture, a needle, a sewing needle, a matting needle, an injection needle, a surgical needle, a safety pin and the like.

Examples of products in pottery (ceramics) industry: products made of pottery, glass, ceramics or enameled products. For example, sanitary potteries (a chamber pot, a wash-bowl, a bathtub, etc.), tableware (a rice-bowl teacup, a dish (plate), a bowl, a teacup, a glass, a bottle, a coffee-pot (siphon), a pan, an earthenware mortar, a cup and the like), vases (a flower bowl, a flowerpot, a bud vase and the like), water tanks (a breeding cistern, an aquarium water tank and the like), chemical experiment appliances (a beaker, a reactor vessel, a test tube, a flask, a laboratory dish, condenser, a mixing rod, a stirrer, a mortar, a bat, a syringe, etc.) a roof tile, enameled ware, an enameled washbowl, and an enameled pan and the like.

Examples of mirrors: a hand mirror, a full-length mirror, a bathroom mirror, a lavatory mirror, vehicle mirrors(a rear-view mirror, a side mirror, a door mirror etc.), half mirror, road mirrors such as a curve mirror, a show window glass, a salesroom in the department store, medical care mirrors, a concave mirror, a convex mirror and the like.

Examples of molding parts: dies for press molding, dies for cast molding, dies for injection molding, dies for transfer molding, dies for compression molding, dies for transfer molding, dies for inflation molding, dies for vacuum molding, dies for blow forming, dies for extrusion molding, dies for fiber spinning, a calendar processing roll and the like.

Examples of ornaments: a watch, a jewel, a pearl, a sapphire, a ruby, an emerald, a garnet, a cat's eye, a diamond, a topaz, a bloodstone, an aquamarine, a turquoise, an agate, a marble, an amethyst, a cameo, an opal, a crystal, a glass, a ring, a bracelet, a brooch, a tiepin (a stickpin), an earring, a necklace, jewelry made of platinum, gold, silver, copper, aluminium, titanium, tin and those alloy, stainless steel, a glass frame and the like.

Examples of forming molds for food: cake, cookies, bread-baking, chocolate, jelly, ice cream, ovenware, an ice tray and the like.

Examples of cookware: kitchen utensils (a pan and a pot), a kettle, a pot, a frying-pan, a hot plate, a toasting net, a takoyaki plate and the like.

Examples of papers: photogravure paper, hydrophobic and oilphobic paper, poster paper, high-grade pamphlet paper, wrapping paper, package paper, drinking package paper, container paper, printing paper, synthtic insulating paper and the like.

Examples of resin(s): a polyolefin such as a polypropylene and polyethylene, a polyvinylchloride plastic, a polyamide, a polyimide, a polyamideimide, a polyester, an aromatic polyester, a polycarbonate, a polystyrene, a polysulfide, a polysulfone, a polyethersulfone, a polyphenylensulfide, a phenolic resin, a furan resin, a urea resin, an epoxy resin, a polyurethane, a silicon resin, an ABS resin, a methacrylic resin, an acrylate resin, a polyacetal, a polyphenylen oxide, a poly methylpentene, a melamine resin, an alkyd resin, an unsaturated polyester cured resin and the like.

Examples of rubber(s): styrene-butadien rubber, butyl rubber, nitril rubber, chloroprene rubber, polyurethane rubber, silicon rubber and the like.

Examples of household electrical appliances: a television, a radio, a taperecorder, an audio, a compact disc (CD), a refrigerator of freezing machines, a freezer, an air conditioner, a juicer, a mixer, a blade of an electric fan, a lighting apparatus, a dial plate, a dryer(or drier) for perm and the like.

Examples of sports articles: skis, fishing rods, poles for pole vaulting, boats, yachts, surfboards, golf balls, bowling balls, fishing line (yarn), fishing nets, floats and the like.

The examples applying to vehicle parts:

(1) ABS resin: a lamp cover, an installment pannel, trimming parts, a protector for a motorcycle.

(2) Cellulose plastic: a car mark, a steering wheel (3) FRP (fiber reinforced plastics): a bumper, an engine cover (jacket)

(4) Phenolic resin: a brake (5) Polyacetal: wiper gear, a gas valve (6) Polyamide: a radiator fan (7) Polyarylate (polycondensation polymerization by bisphenol A and pseudo phtalic acid): a direction indicator lamp (or lense), a cowl board lense, a relay case (8) Polybutylene terephtalate (PBT): a rear end, a front fender (9) Poly(amino-bismaleimide): engine parts, a gear box, a wheel, a suspension drive system

(10) Methacrylate resin: a lamp cover lens, a meter pannel and its cover, center mark

(11) Polypropylene: a bumper

(12) Polyphenylen oxide:a radiator grille, a wheel cap

(13) polyurethane: a bumper, a fender, an installment pannel, a fan

(14) Unsaturated polyester resin: a body, a fuel tank, a heater housing, a meter pannel.

Examples of office supplies: a fountain pen, a ballpoint pen, a propelling pencil (an automatic or a mechanical pencil), a pencil case, a binder, a desk, a chair, a bookshelf, a rack, a telephone stand table, a rule (measure), a drawing instrument and the like.

Examples of building materials: materials for a roof, and outer wall and interiors. Roof materials such as brick, slate and tin (a galvanized iron sheet) and the like. Outer wall materials such as wood (including processed manufactured wood), mortar, concrete, ceramics sizing, metalic sizing, brick, stone, plastics and metal like aluminium. Interior materials such as a wood (indluding a processed wood), a metal like aluminium, plastic, paper, fiber and the like.

Examples of building stones: granite, marble and others used for use as a building, a building material, an architecture, an ornament, a bath, a gravestone, monument, a gatepost, a stone wall, a paving stone etc.

Examples of musical instruments and sound apparatus: a percussion instrument, a stringed instrument, a keyboard instrument, a woodwind instrument, the brass and others, and sound apparatus such as a microphone, a speaker. To be concrete, there are musical instrumentos such as a drum, a cymbal, a violin, a cello, a guitar, a koto (harp), a piano, a flute, a clarinet, a bamboo flute and a horn, and sound apparatus such as a microphone, a speaker and a ear-phone and the like.

Examples of a thermos bottle, a vacuum bottle, a vacuum vessel and the like.

Examples of a highly resisiting voltage insulator such as a power supplying insulator or a spark plug, which have a highly hidrophobic, oilphobic and prevention of contamination properties.

Now, examples of the method of lamination of an organic monomolecular film according to the invention and the chemical adsorption agent used for the same method will be described with reference to FIGS. 1 to 4.

EXAMPLE 1

As shown in FIG. 1(a), by dipping the substrate 1 (for example Al) having a small quantity of hydrophilic OH groups exposed on its surface, in a solution obtained by dissolving 1% wt of $SiCl_4$, as the material containing a trichlorosilyl group in a molecule, in chloroform, a hydrochloric acid removal reaction was brought about on the substrate surface as shown in FIG. 1(b), as given by the following formula [1];

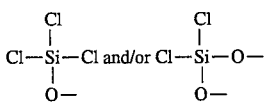

formula [1]

whereby molecules are fixed to the substrate surface via —SiO— bonds.

By subsequently washing the substrate with a non-aqueous solvent, for instance chloroform, and then with water, $SiCl_4$ molecules remaining without reaction with the substrate were removed to obtain a siloxane monomolecular film 4 on the substrate surface as shown in FIG. 1(c) and given as the following formula [2];

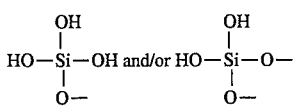

formula [2]

The monomolecular film 4 thus obtained was perfectly bonded by chemical bonds of —SiO— to the substrate and never separated from the substrate.

In addition, it has many —SiOH bonds on its surface since, about three times of the initial number of hydroxyl groups on the surface of the substrate 1 were produced.

Andthen, by dipping the substrate for 30 min. in the solution containing a material presented by the formula: $CF_3(CF_2)_7(CH_2)_2SiCl_3$ at a concentration of 2.0% wt in a soluvent containing 80 % wt n-hexadecane. 12% wt of carbon tetrachloride and 8% wt of chloroform as the material with a fluorocarbon group and a chlorosilane group in molecule, a monomolecular film 5 presented by the formula [3];

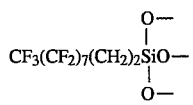

formula [3]

was formed on the substrate surface. The monomolecular film 5 containing fluorine was also bonded to the inner siloxane monomolecular film 4 by covalent bonds as shown in FIG. 1(d).

Thus, the monomolecular film was never separated in a checkerboard test.

While, in the above example $CF_3(CF_2)_7(CH_2)_2SiCl_3$ was used as the fluorocarbon-based surface active agent, by adding a C=C or C≡C group to or assembling it in an alkyl chain portion, cross-linking can be obtained by irradiation with an electron beam of the order of 5 Mrads, thus permitting further improvement of the hardness.

As the fluorocarbon-based surface active agent;

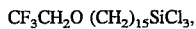

$CF_3CH_2O(CH_2)_{15}SiCl_3$,

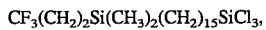

$CF_3(CH_2)_2Si(CH_3)_2(CH_2)_{15}SiCl_3$,

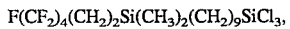

$F(CF_2)_4(CH_2)_2Si(CH_3)_2(CH_2)_9SiCl_3$,

$CF_3COO(CH_2)_{15}SiCl_3$ may be used in addition to the agent noted above. With any of these agents, satisfactory results could be obtained.

Further, the invention is never limited to fluorine-containing systems; for instance, it can be usefully applied to super-thin protective films having mechanical strength. In such cases, fluorine is not essential.

EXAMPLE 2

A back mirror 11 made of an acrylate resin permitting weight reduction of the car, which was hydrophobic was treated in a plasma atmosphere containing oxygen at 100 W for 20 min. And then, it was dipped for about 30 minutes in a solution obtained by dissolving a material represented by the formula [4] of 1% wt,

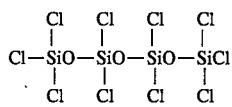

formula [4]

as a material containing a chlorosilyl group in molecule in a fleon 113 solvent as a non-aqueous solvent. As a result, a hydrochloric acid removal reaction was brought about on the surface of the back mirror 11 owing to some hydrophilic —OH groups 12 produced by the plasma treatment on the surface, and a chlorosilane monomolecular film from the material containing a trichlorosilyl group in molecule was formed. By using the material represented by the formula [4] as the material containing a trichlorosilyl group in molecule as in the above way, the hydrochloric acid removal reaction is brought about on the surface of the back mirror 11 with only a small amount of hydrophilic OH groups on the surface of the back mirror 11. Thus, the molecules as represented by the formula [4] are fixed via —SiO— bonds to the surface.

Usually, on the chlorosilane monomolecular film thus obtained non-reacted the formula [4] are present. Therefore, the treated mirror was subsequently washed with a fleon 113 solvent solution to remove the formula [4] remaining without reaction with hydroxyl groups on the surface of the back mirror 11 and then with water, thus obtaining a siloxane monomolecular film 13 as represented on the surface of the back mirror 11 as formula [5] and/or formula [6].

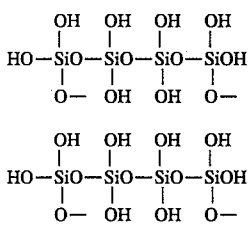

formula[5]

formula[6]

The monomolecular film 13 thus obtained is perfectly bonded via covalent bonds of —SiO— to the surface of the back mirror 11 and thus never separated. It also increased has a great number of —SiOH bonds on its surface.

Figure 4:
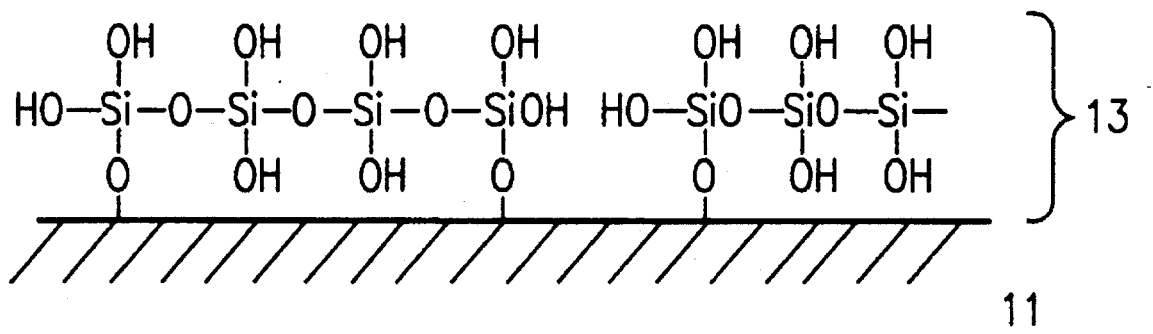

The back mirror 11 with the siloxane monomolecular film 13 formed thereon was held dipped for about one hour in the solution noted before in Example 1. As a result, a monomoleclar film represented by the formula [3] was laminated on the surface of the siloxane monomolecular film 13 as shown in FIG. 4. A chemically adsorbed monomolecular film 14 containing fluorine was formed with a thickness of about 1.5 nm on the entire mirror surface, and it was also chemically bonded to the inner siloxane monomolecular film 13.

Thus, the monomolecular film was never separated in a separation test.

The treated back mirror in this example was trial used.

Owing to the hydrophilic fluorine on the surface, no attached water drop could be found. Touching the back mirror surface with hair, hair oil was attached little to the surface.

In Example 1, a single silane-based surface active agent layer containing fluorine was laminated on a single siloxane-based monomolecular film. However, the same effects of the invention are obtainable by laminating any desired number of chemically adsorbed monomolecular films.

EXAMPLE 3

The same experiment as in Example 2 was conducted except for using an polycarbonate resin substrate instead of the acrylic resin substrate, using tridecafluorooctyltrichlorosilane $[CF_3(CF_2)_5CH_2CH_2SiCl_3]$ nstead of heptadecafluorodecyl-trichlorosilane $[CF_3(CF_2)_7(CH_2)_2SiCl_3]$ and using 1,1-diclhoro-2,2,3,3,3-pentafluoropropane instead of fleon 113.

EXAMPLE 4

The same experiment as in Example 1 was conducted except for using a stainless steel substrate instead of the Al substrate and using tridecafluorooctyltrichlorosilane instead of heptadecafluorodecyltrichlorosilane.

EXAMPLE 5

The same experiment as in Example 2 was conducted except for using an ABS resin substrate instead of the acrylate resin substrate.

EXAMPLE 6

The same experiment as in Example 2 was conducted except for using an epoxy resin substrate instead of the acrylate resin substrate.

EXAMPLE 7

The same experiment as in Example 2 was conducted except for using a polyurethane resin substrate instead of the acrylate resin substrate.

EXAMPLE 8

The same experiment as in Example 2 was conducted except for using a butadiene-styrene rubber substrate instead of the acrylate resin substrate and using 1,1-dicyclo 2,2,3,3,3-pentafluoropropane instead of fleon 113.

EXAMPLE 9

The same experiment as in Example 2 was conducted except for using a butyl rubber substrate instead of the acrylate resin substrate and using 1,1-dicyclo-2,2,3,3,3-pentafluoropropane instead of fleon 113.

EXAMPLE 10

The same experiment as in Example 2 was conducted except for using a nitrile rubber substrate instead of the acrylate resin substrate and using 1,1-dicyclo-2,2,3,3,3-pentafluoropropane instead of fleon 113.

EXAMPLE 11

A chemically adsorbed monomolecular film was formed in the manner as in Example 2 except for using 18-nonadecenyltrichlorosilane instead of heptadecafluorodecyltrichlorosilane, followed by irradiation with a 300-keV 0.02-Mrads electron beam in a Nitrogen atmosphere for one minute.

EXAMPLE 12

The same experiment as in Example 2 was conducted except for using tetracyclosilane instead of heptadecafluorodecyl-trichlorosilane.

EXAMPLE 13

The same experiment as in Example 2 was conducted except for adopting, instead of the oxidation method, a method, in which the substrate was dipped for 5 minutes in concentrated sulfuric acid containing 10% wt. of potassium dichromate.

COMPARATIVE EXAMPLE 1

A polycarbonate substrate was spin coated with a methanol solution containing 2% wt of a silane-based coupling agent (i.e., heptadecafluorodecyltrimethoxysilane), followed by drying at 20° C. for one hour.

COMPARATIVE EXAMPLE 2

On the polycarbonate substrate in Example 2 was formed a chemically adsorbed monomolecular film of heptadecafluorodecyl-trichlorosilane without carrying out any oxidation treatment.

COMPARATIVE EXAMPLE 3

The polycarbonate substrate in Example 2 was spin coated with a suspension of polytetrafluoroethylene, followed by thermal drying at 120° C. for one hour.

The contact angle of each of the samples of Examples 1 to 13 and Comparative examples 1 to 2 with respect to super-pure water and also to salad oil was examined. It was measured immediately after the formation of the chemically adsorbed film or coating film and also after subsequently rubbing the surface 10,000 times with cloth wetted with water. Table 1 shows the results.

TABLE 1

| | Contact angle (°) with respect to water | | Contact angle (°) with respect to salad oil | |
|---|---|---|---|---|
| | Initial value | After test | Initial value | After test |
| Ex. 1 | 120 | 118 | 95 | 92 |
| Ex. 2 | 115 | 111 | 93 | 81 |
| Ex. 3 | 112 | 110 | 93 | 91 |
| Ex. 4 | 113 | 111 | 93 | 91 |
| Ex. 5 | 111 | 109 | 92 | 90 |
| Ex. 6 | 111 | 110 | 91 | 90 |
| Ex. 7 | 110 | 109 | 90 | 88 |
| Ex. 8 | 111 | 110 | 91 | 90 |
| Ex. 9 | 112 | 110 | 92 | 90 |
| Ex. 10 | 111 | 109 | 91 | 89 |
| Ex. 11 | 108 | 104 | 90 | 82 |
| Ex. 12 | 107 | 103 | 89 | 81 |
| Ex. 13 | 112 | 110 | 92 | 90 |
| Com. ex. 1 | 93 | 45 | 61 | 12 |
| Com. ex. 2 | 45 | 45 | 12 | 12 |

As seen from Table 1, the polymer compositions according to the invention retained the hydrophobic and oil-repelling properties or were hydrophobic even after repeated washing of the surface with water-containing cloth. On the other hand, the samples of Comparative examples no longer retained the hydrophobic and/or oil-repelling properties. The sample of comparative example 2, with which the surface of the polymer composition had not been treated for oxidation, was incapable of formation of a chemical adsorption film having siloxane bonds.

Among the polymer compositions according to the invention, those provided with chemical adsorption monomolecular film containing fluoroalkyl groups excellently prevented contamination. After the friction test, the sample of Example 2 was dipped in salad oil, and oil attached in this way could be perfectly wiped off with tissue paper. With the sample of Comparative example 1, on the other hand, the surface was sticky with an oil film remaining on its surface even after wiping the surface many times with tissue paper.

The polymer composition according to the invention can be utilized as optical material as well. With the polycarbonate substrate in Example 3, the permeability of visible light was 92%, which was the same as the value before the formation of the chemical adsorption monomolecular film. With the sample of Comparative example 3, coated with polytetrafluoroethylene, the permeability of visible light was reduced to 50% or below, as inferior as that of frosted glass.

While any of the above examples concerned the formation of a single monomolecular film, a polymer composition which was obtained by laminating chemical adsorption monomolecular films or a chemical adsorption film obtained without removal of the non-reacted chlorosilane surface active agent provided the same function. Further, while any of the above examples used a substrate composed of a sole polymer as a polymer-containing substrate, polymers containing fillers, plasticizers, coloring agents, etc. permitted to obtain the same functions as imparted to polymer compositions.

Example 14

This example concerns a knife, which contains less hydroxyl groups although it is hydrophilic. Such a knife may be made of such metal as aluminum, copper or stainless steel, or it may be a plastic knife with the surface made hydrophilic. A knife made of a plastic material in situ, i.e., without any oxide film on the surface, may be treated in advance to make the surface hydrophilic, i.e., introduce hydroxyl groups. This may be done so by treating the surface in an oxygen-containing plasma atmosphere at 100 W for 20 minutes. for instance.

By dipping such a knife for about 30 minutes in a non-aqueous solution containing a material containing a plurality of chlorosilyl groups in molecule (for instance $SiCl_4$, $SiHCl_3$, $SiH_2Cl_2$ or $Cl-(SiCl_{2O})_n SiCl_3$, n being an integer, preferably $SiCl_4$ having a small molecular size, high activity to the hydroxyl group and hence being highly effective for making the knife surface uniformly hydrophilic), for instance a solution prepared by dissolving 1% wt of the material noted above in a chloroform solvent, a hydrochloric acid removal reaction is brought about on the knife surface owing to some hydrophilic —OH groups present on the surface, whereby is formed a chlorosilane monomolecular film from the material containing a plurality of chlorosilyl groups in molecule.

For example, by using $SiCl_4$ as the material having a plurality of trichlorosilyl groups in molecule a hydrochloric acid removal reaction is brought about on the knife surface owing to a small amount of hydrophilic 0H groups exposed on the surface to fix molecules to the surface via —SiO— bonds such as $Si(Cl)_3O$— or —$OSi(Cl)_2O$—.

And then, the knife is washed by the fleon 113 to removing the material remaing on the surface without reaction, followed by washing by water, the —SiCl group changed to —SiOH group.

The monomolecular film having many hydroxyl groups thus formed is perfectly bonded to the knife via covalent bonds of —SiO—. It is never separated so long as no decomposition reaction takes place. Its surface has a great number of —SiOH bonds, the number corresponding to about three times of the initial number of hydroxyl groups.

By dipping the knife which had the aforementioned monomolecular film having a great number of —SiOH groups and formed on its surface, in a non-aqueous solution containing $CF_3(CF_2)_7(CH_2)_2SiCl_3$ at a concentration of 1% wt, in a solvent containing 80% wt n-hexadecane, 12% wt of carbon tetrachloride and 8% wt chloroform for one hour.

As a result, bonds of $CF_3(CF_2)_7(CH_2)_2Si(O-)_3$ were formed on the knife surface, and a fluorine-containing monomolecular film was formed to a thickness of about 2.0 nm on the entire surface of the knife such that it was chemically bonded to the inner siloxane monomolecular film. This fluorocarbon-based monomolecular film was never separated in a checkerboard test.

EXAMPLE 15

This example concerns porcelain dish, which contains less hydroxyl groups although it is hydrophilic. By dipping such porcelain dish for about 30 minutes in a non-aqueous solution containing a material with a plurality of chlorosilyl groups in molecule (for instance $SiCl_4$ having a small molecular size and highly active with respect to the hydroxyl group and thus highly effective for uniformly making the porcelain surface hydrophilic), for instance a solution prepared by dissolving 1% wt of the material noted above in a chloroform solvent, a hydrochloric acid removal reaction is brought about on the surface owing to some hydrophilic —OH groups present on the porcelain surface, and thus a chlorosilane monomolecular film from the material containing a plurality of chlorosilyl groups in molecule.

For example, by using $SiCl_4$ as the material containing a plurality of chlorosilyl groups, a hydrochloric acid removal reaction is brought about on the porcelain dish surface owing to a small amount of hydrophilic —OH groups exposed on the porcelain surface to fix molecules to the surface via —SiO— bonds such as $Si(Cl)_3O-$.

And then, the porcelain dish is washed by the fleon 113 to removing the material remaing on the surface without reaction, followed by washing by water, the —SiCl group changed to —SiOH group.

The monomolecular film thus obtained is perfectly bonded to the surface via covalent bonds of —SiO— and thus is never separated. It has a great number of —SiOH groups on its surface, the number corresponding to about three times of the initial number of hydroxyl groups.

By dipping the porcelain dish which had the aforementioned monomolecular film having a great number of —SiOH groups and formed on its surface, in a non-aqueous solution containing $CF_3(CF_2)$ ? $(CH_2)_2SiCl_3$ at a concentration of 1% wt, in a solvent containing 80% wt n-hexadecane, 12% wt of carbon tetrachloride and 8% wt chloroform for one hour.

As a result, bonds of $CF_3(CF_2)_7(CH_2)_2Si(O-)_3$ were produced on the porcelain dish surface, and a fluorine-containing monomolecular film was formed to a thickness of about 2.0 nm on the entire surface of the porcelain dish such that it was chemically coupled to the inner siloxane-based monomolecular film. This fluorcarbon-based monomolecular film was never separated in a separation test.

EXAMPLE 16

This example concerns a metal pan such as an aluminum or stainless steel pan, which contains less hydroxyl groups although it is hydrophilic. By dipping such a metal pan for about 30 minutes in a non-aqueous solution containing a material containing a plurality of trichlorosilyl groups (for instance $SiCl_4$), for instance a solution prepared by 1% wt of the above material in a chloroform solvent, a hydrochloric acid removal reaction is brought about on the surface, and a chlorosilane monomolecular film of the material containing a plurality of chlorosilyl groups is formed.

For example, by using $SiCl_4$ as the material containing a plurality of chlorosilyl groups, a hydrochloric acid removal reaction is brought about on the surface owing to a small amount of —OH groups exposed on the surface to fix molecules to the surface via —SiO— bonds as represented as above formula [1].

By subsequently washing the pan with a non-aqueous solvent. e.g., chloroform, and then with water. $SiCl_4$ molecules remaining without reaction with the pan material surface are removed to obtain a siloxane-based monomolecular film as represented as above formula [2] on the pan surface.

The monomolecular film having many hydroxyl groups thus formed is perfectly bonded to the pan via covalent bonds of —SiO— and is thus never separated. It has a great number of —SiOH bonds on the surface, the number corresponding to about three times of the initial number of hydroxyl groups.

By dipping the pan which had the aforementioned monomolecular film having a great number of —SiOH groups and formed on its surface, in a non-aqueous solution containing $CF_3(CF_2)_7(CH_2)_2SiCl_3$ at a concentration of 1% wt, in a solvent containing 80% wt n-hexadecane, 12% wt of carbon tetrachloride and 8% wt chloroform for one hour.

As a result, bonds of $CF_3(CF_2)_7(CH_2)_2Si(O-)_3$ were produced on the pan surface, and a fluorine-containing monomolecular film was formed to a thickness of about 1.5 nm on and over the entirety of the pan surface such that it was chemically bonded to the inner siloxane monomolecular film. This monomolecular film was never separated in a separation test.

EXAMPLE 17

This example concerns a porcelain coffee cup which contains less hydroxyl groups although it is hydrophilic. By dipping the porcelain coffee cup for about 30 minutes in a non-aqueous solution containing a material containing a plurality of trichlorosilyl groups (for instance $SiCl_4$), for instance a solution prepared by 1% wt of the above material in a chloroform solvent, a hydrochloric acid removal reaction is brought about on the surface, and a chlorosilane monomolecular film of the material containing a plurality of chlorosilyl groups is formed.

For example, by using SiCl$_4$ as the material containing a plurality of chlorosilyl groups, a hydrochloric acid removal reaction is brought about on the surface owing to a small amount of —OH groups exposed on the surface to fix molecules to the surface via —SiO— as represented as above formula [1].

By subsequently washing the coffee cup with a non-aqueous solvent. e.g., chloroform, and then with water, SiCl$_4$ molecules remaining without reaction with the coffee cup material surface are removed to obtain a siloxane-based monomolecular film as represented as above formula [2] on the coffee cup surface.

The monomolecular film having many hydroxyl groups thus formed is perfectly bonded to the coffee cup via covalent bonds of —SiO— and is thus never separated. It has a great number of —SiOH bonds on the surface, the number corresponding to about three times of the initial number of hydroxyl groups.

By dipping the coffee cup which had the aforementioned monomolecular film having a great number of —SiOH groups and formed on its surface, in a non-aqueous solution containing CH$_3$(CH$_2$)$_{11}$SiCl$_3$ at a concentration of 1% wt, in a solvent containing 80% wt n-hexadecane, 12% wt of carbon tetrachloride and 8% wt chloroform for one hour.

As a result, bonds of

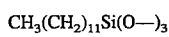

were produced on the coffee cup surface, and a hydrocarbon monomolecular film was formed to a thickness of about 1.7 nm on and over the entirety of the coffee cup surface such that it was covalent bonded to the inner siloxane monomolecular film. This monomolecular film was never separated in a separation test.

As has been described in the foregoing, the invention concerns a chemically adsorbed monomolecular lamination film, which comprises a chemically adsorbed monomolecular film formed on a substrate surface via a siloxane-based monomolecular or polymer film, and a method of manufacturing a chemically adsorbed monomolecular lamination film, which comprises a step of contacting a substrate containing hydroxyl groups present on the surface with a non-aqueous solution containing a material having a chlorosilane group in molecule, a step of removing the material remaining on the substrate without reaction by washing the substrate with a non-aqueous organic solution (if this process is omitted, the siloxane-based polymer film is prepared on the substrate), a step of forming a monomolecular film constituted by a compound containing a silanol group in molecule on the substrate by exposing the substrate to air containing moisture washing with water after the removal step, and a step of laminating a monomolecular adsorption film by causing chemical adsorption of a chlorosilane-based surface active agent constituted by straight hydrocarbon chain and/or fluorocarbon-based molecules each having a chlorosilane group at one end onto the substrate after on the siloxane-based monomolecular film formation step. Thus, it is possible to obtain effective lamination film of a chemically adsorbed monomolecular film even with metal or plastic substrates having few hydroxyl groups present on the surface.

Thus, by using a compound containing a fluorocarbon group and a chlorosilyl group in molecule, a fluorocarbon-based monomolecular film having excellent hydrophilic and oil-repelling properties may be formed on even such a metal substrate as Al, Cu and stainless steel substrates in a state chemically bonded to the substrate, at a high density, pin-hole-free, with a uniform thickness and very thinly. It is thus possible to provide a very highly durable, high performance and super-thin fluorocarbon-based film.

Further, the chemically adsorbed monomolecular film according to the invention may be used for apparatuses or the like requiring heat-resistant, weather-resistant and wear-resistant super-thin film coatings such as electronic products, particularly such electric products as hot plates and rice cookers, vehicles, industrial apparatuses, mirrors and glass lenses.

As has been shown, the invention is greatly beneficial to the industry.

The invention may be embodied in other specific forms without departing from the spirit or essential characteristics thereof. The present embodiment is to be considered in all respects as illustrative and not restrictive, the scope of the invention being indicated by the appended claims rather than by the foregoing description and all changes which come within the meaning and range of equivalency of the claims are intended to be embraced therein.

We claim:

1. A method of manufacturing a chemically adsorbed monomolecular lamination film comprising:

contacting a substrate having hydroxyl groups on the surface with a non-aqueous solution containing a material having plural chlorosilane groups;

removing said unreacted material remaining on the substrate by washing the substrate using a non-aqueous organic solvent;

forming on the substrate a siloxane-based film comprising a compound containing a silanol group by reacting the chlorosilane groups with water after said removing step; and adsorbing a chlorosilane-based surface active agent having a straight hydrocarbon chain and a chlorosilane group at one end onto the substrate after said siloxane-based film forming step to form the adsorbed monomolecular lamination film.

2. The method of manufacturing a chemically adsorbed film lamination film according to claim 1, wherein the substrate is made selected from the member of a group consisting of metals and ceramics.

3. The method of manufacturing a chemically adsorbed monomolecular lamination film according to claim 1, wherein the substrate is a plastic substrate with the surface having been made hydrophilic in advance by a treatment in a plasma or corona atmosphere containing oxygen.

4. The method of manufacturing a chemically adsorbed monomolecular lamination film according to claim 1, wherein said material having plural chlorosilane groups is selected from the group consisting of SiCl$_4$, SiHCl$_3$, SiH$_2$Cl$_2$ and Cl—(SiCl$_2$O)$_n$—SiCl$_3$ where n is an integer.

5. The method of manufacturing a chemically adsorbed monomolecular lamination film according to claim 1, wherein the hydrocarbon chain of said chlorosilane-based surface active agent is partly substituted for by a —CF$_2$— group.

6. The method of manufacturing a chemically adsorbed monomolecular lamination film according to claim 1, wherein said chlorosilane-based surface active agent is CF$_3$—(CF$_2$)$_n$—(R)$_m$—SiX$_p$Cl$_{3-p}$ where n represents 0 or an integer, R represents an alkyl group or a substitute group containing a C=C, a C≡C, a silicon atom or an oxygen atom, m represents 0 or 1, X represents a hydrogen atom or a substitute group selected from the group consisting of an alkyl group, an alkoxy group, a fluorine-containing alkyl group and a fluorine-containing alkoxy group, and p represents 0, 1 or 2.

7. The method of manufacturing a chemically adsorbed monomolecular lamination film according to claim 5, wherein said chlorosilane-based surface active agent is $CF_3$—$(CF_2)_n$—$(R)_m$—$SiX_pCl_{3-p}$ where n represents 0 or an integer, R represents an alkyl group or a substitute group containing a C=C, a C≡C, a silicon atom or an oxygen atom, m represents 0 or 1, X represents a hydrogen atom or a substitute group selected from the group consisting of an alkyl group, an alkoxy group, a fluorine-containing alkyl group and a fluorine-containing alkoxy group, and p represents 0, 1 or 2.

8. A method of manufacturing a chemically adsorbed monomolecular lamination film comprising:

contacting a substrate having hydroxyl groups on the surface with a non-aqueous solution containing a material having plural chlorosilane groups;

forming on the substrate a siloxane-based film comprising a compound containing a silanol group by reacting the chlorosilane groups with water after said removing step; and adsorbing a chlorosilane-based surface active agent having a straight hydrocarbon chain and a chlorosilane group at one end onto the substrate after said siloxane-based film forming step to form the adsorbed monomolecular lamination film.

\* \* \* \* \*